United States Patent [19]

Boissinot et al.

[11] Patent Number: 4,553,992
[45] Date of Patent: Nov. 19, 1985

[54] SCRUBBER APPARATUS FOR PURIFYING FOUL AIR PRODUCED DURING AN EMBALMING, AN AUTOPSY OR THE LIKE

[76] Inventors: Jean-Guy Boissinot, 146 rue du Golf, Loretteville, (Quebec), Canada, G2A 1G6; Pierre Begin, 19 rue Bèlair, Apt. 103, Levis, (Quebec), Canada, G6V 6K9

[21] Appl. No.: 661,919

[22] Filed: Oct. 17, 1984

[51] Int. Cl.⁴ .............................................. B01D 39/00
[52] U.S. Cl. ........................................ 55/279; 55/470; 55/524; 55/316; 98/115.1; 98/115.3; 126/299 D; 422/121
[58] Field of Search ................. 55/279, 467, 470, 524, 55/316; 126/299 D; 422/4, 5, 24, 121; 98/115 R, 115 LH, 115.1, 115.3; 27/1, 23; 128/1 R, 139

[56] References Cited

U.S. PATENT DOCUMENTS

| | | | |
|---|---|---|---|
| 2,369,375 | 2/1945 | Sonntag | 55/279 |
| 2,886,124 | 5/1959 | Scharmer | 55/316 |
| 3,064,551 | 11/1962 | Stalker | 126/299 D |
| 3,230,033 | 1/1966 | Hamilton et al. | 422/121 |
| 3,496,704 | 2/1970 | Bandlow | 126/299 D |
| 3,674,421 | 7/1972 | Decupper | 422/121 |
| 3,744,216 | 7/1973 | Halloran | 55/524 X |
| 4,227,904 | 10/1980 | Kasmark et al. | 55/316 |

Primary Examiner—Charles Hart
Attorney, Agent, or Firm—Robic, Robic & Associates

[57] ABSTRACT

An air scrubber apparatus which purifies foul air produced during an embalming or an autopsy carried out on a work table disposed in a room. The scrubber apparatus comprises a housing positioned above the work table, this housing having a first and a second side corresponding to a first and a second side of the work table, respectively. The housing defines from its first side to its second side a first longitudinal outer compartment provided at its two ends with outlets to the room, a central compartment having no bottom wall for thereby providing this central compartment with a wide bottom opening to the room, and a second longitudinal outer compartment also provided at its two ends with outlets to the room. An air filter designed to allow passage of air therethrough is positioned over the bottom opening of the central compartment and comprises a filtering material, including aluminum oxide and potassium permanganate, which filtering material allowing purifying of the foul air upon passage thereof through the air filter. A first and a second fan move the foul air towards the interior of the central compartment through the air filter for the purpose of purifying this foul air. The first fan transfers the purified air from the central compartment to the first outer compartment and the second fan transfers this purified air from the central compartment to the second outer compartment to thereby redistribute the purified air in the room through the end outlets of the first and second longitudinal outer compartments. An ultraviolet ray tube may also be mounted in the central compartment or in both the first and second outer compartments to kill germs, bacteria and the like present in the purified air. In order to increase the efficiency of the scrubber apparatus, a plexiglass wall structure may also be provided between the housing and the work table. The use of the scrubber apparatus is not limited to embalming and autopsy. It can of course be used for any other purpose provided that malodorous, pungent and/or corrosive gaseous substances similar to those inherent to embalming and autopsy or which can be removed by the air filter of the scrubber apparatus are mixed to the ambient air to produce foul air.

19 Claims, 7 Drawing Figures

SCRUBBER APPARATUS FOR PURIFYING FOUL AIR PRODUCED DURING AN EMBALMING, AN AUTOPSY OR THE LIKE

The present invention relates to an air scrubber apparatus designed for purifying foul air produced during, for example, an embalming or an autopsy carried out on a work table in an embalming or autopsy room.

It should be pointed out that the use of the scrubber apparatus of the invention is not limited to its use for embalming and autopsy. Indeed, it can be used for any other purpose provided that malodorous, pungent and/or corrosive gaseous substances similar to those inherent to embalming and autopsy or which can be removed by air filter means of the scrubber apparatus of the invention are mixed to the ambient air, thereby rendering necessary a cleaning of the ambient air from such gaseous substances in order to keep breathable the air in the room.

In conventional autopsy or embalming rooms, exhaust fans are provided to evacuate the produced foul air to the outside. An important drawback of such exhaust fans is that, while evacuating to the outside the foul air, heated or cooled air is also evacuated thereby greatly increasing the heating and conditioning costs.

A solution to this drawback, is to use an air scrubber apparatus which returns the air to the room after purification thereof. Some apparatuses of this type are proposed for example in U.S. Pat. Nos. 3,844,741 (DIMITRIK), 3,846,072 (PATTERSON), 4,118,191 (BOHNENSIEKER), and 4,252,547 (JOHNSON). However, none of these apparatuses is adapted for its use in a room to carry out, for example, embalming or autopsy An object of the present invention is therefore to provide an air scrubber apparatus which may be used in association with a work table in an embalming or autopsy room, and which eliminates the above-mentioned drawback of the conventional exhaust fans.

More specifically, according to the present invention, there is provided an air scrubber apparatus for purifying foul air produced during an embalming, an autopsy or the like carried out on a work table disposed in a room for embalming, autopsy or the like, comprising:

a housing positioned above the work table, this housing defining a first and a second outer compartment disposed substantially horizontally with respect to each other, the housing also defining a central compartment disposed between the first and second outer compartments, this central compartment being provided with bottom inlet opening means for the foul air, and the first and second outer compartments being each provided with outlets to the room which are located at predetermined positions;

air filter means positioned over the bottom inlet opening means of the central compartment, these filter means comprising a filtering material including aluminium oxide and potassium permanganate and being designed to allow passage of air therethrough, the filtering material which includes aluminium oxide and potassium permanganate purifying the foul air upon passage thereof through the filter means; and air pumping means for moving the foul air towards the interior of the central compartment through the filter means for the purpose of purifying this foul air, such pumping means comprising means for transferring the purified air from the central compartment to the first and second outer compartments in order to return the purified air to the room through the outlets of these first and second outer compartments, the predetermined positions of these outlets being selected so as to enable a redistribution of the purified air in the room.

Preferably, the air scrubber apparatus comprises means for killing germs, bacteria and the like present in the purified air. These killing means may comprise an ultraviolet ray tube mounted in the central compartment. Alternatively, the killing means may comprise a first ultraviolet ray tube mounted in the first outer compartment, and a second ultraviolet ray tube mounted in the second outer compartment.

The objects, advantages and other features of the present invention will become more apparent from the following non restrictive description of preferred embodiments thereof, made with reference to the accompanying drawings in which.

Figure 1:
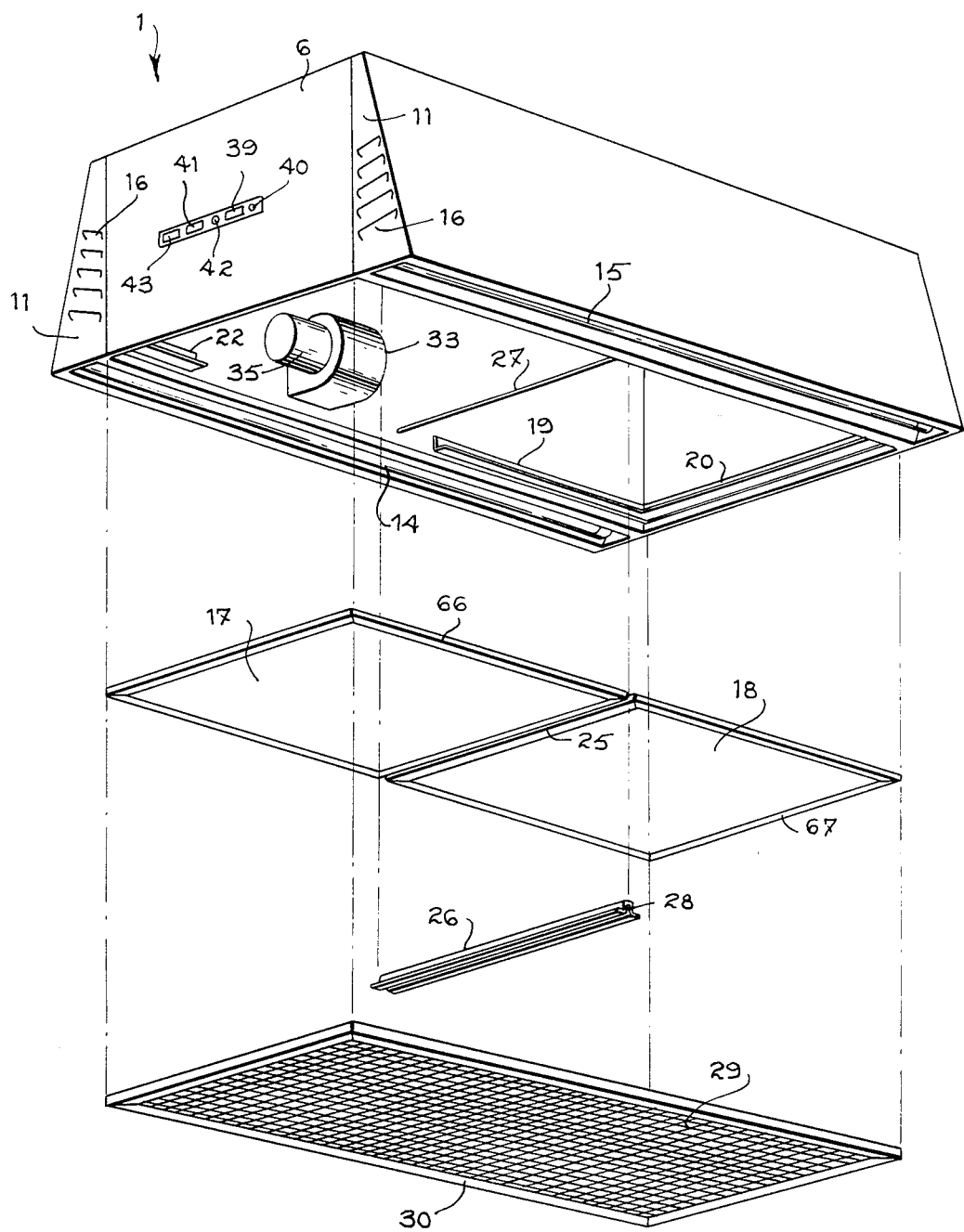
FIG. 1 is an explosion view of a first embodiment of the air scrubber apparatus according to the invention.
Figure 4:
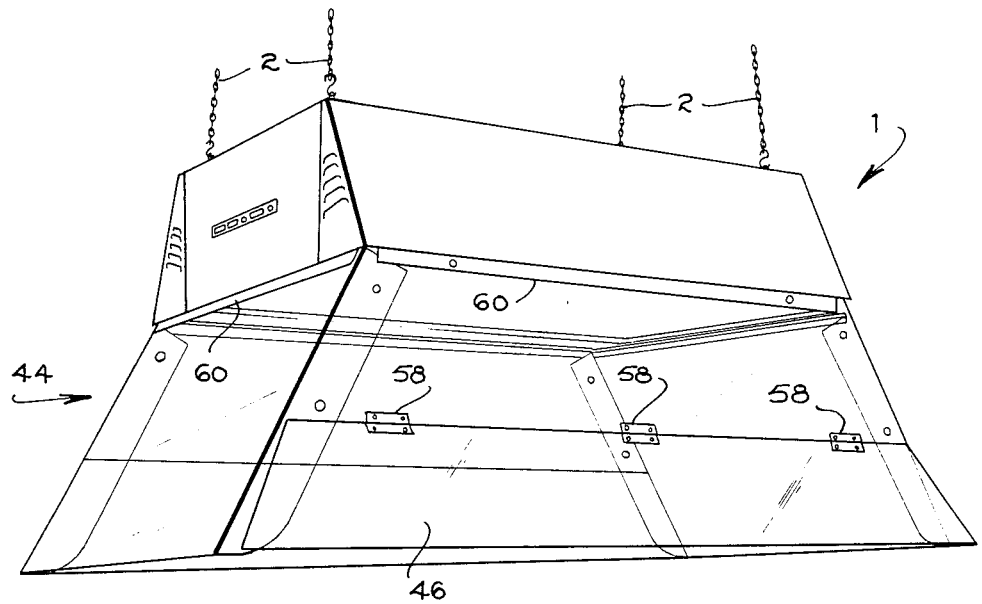
Figure 5:
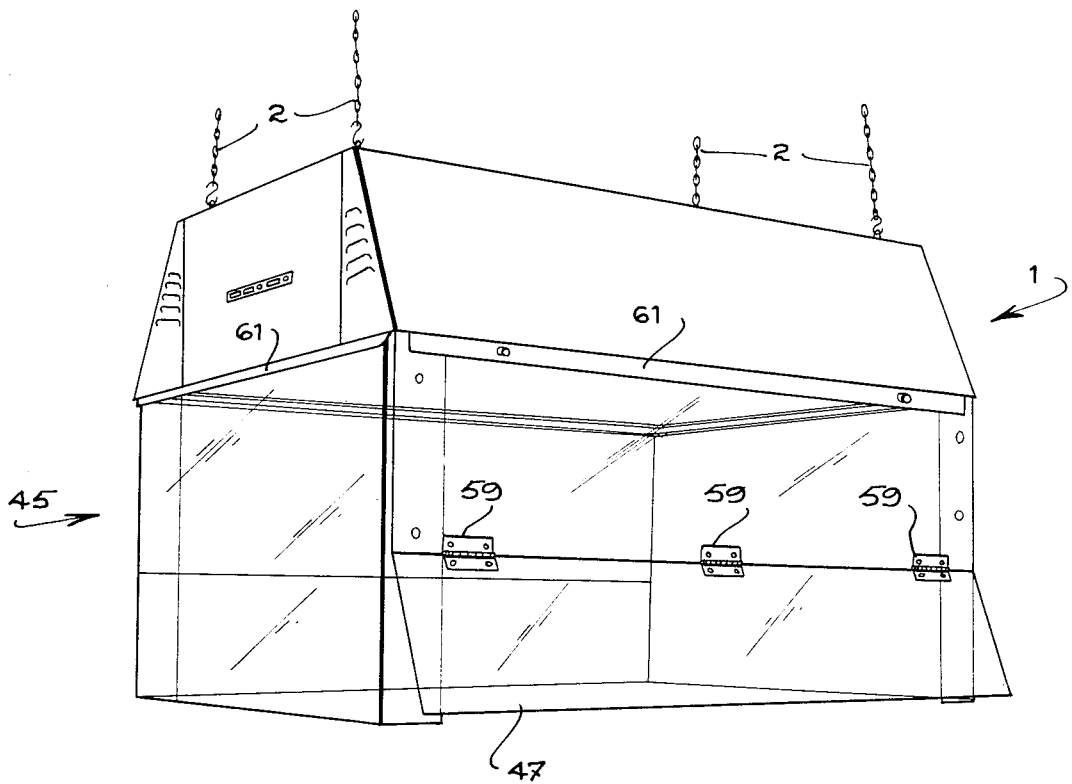
Figure 6:
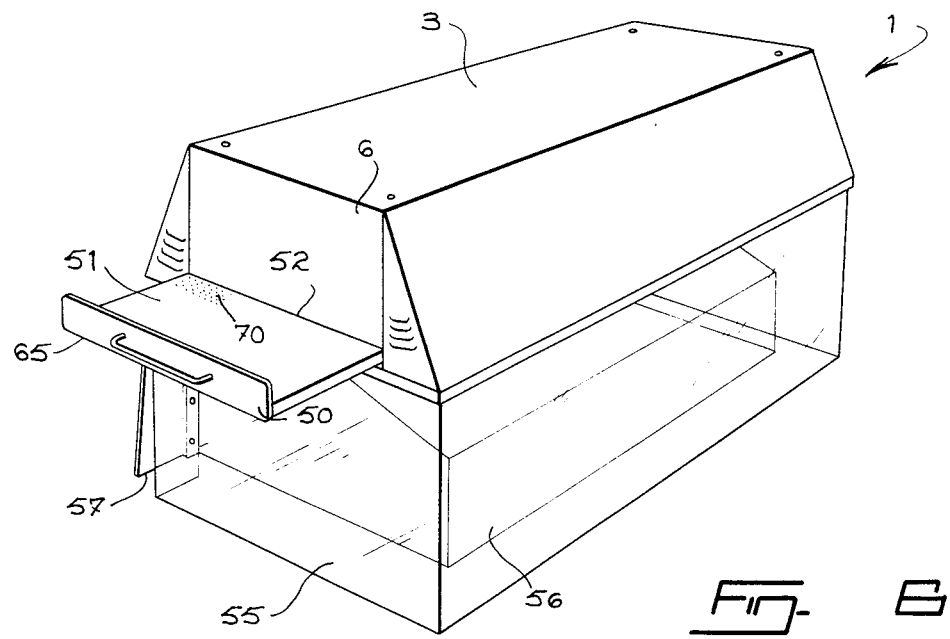
Figure 7:
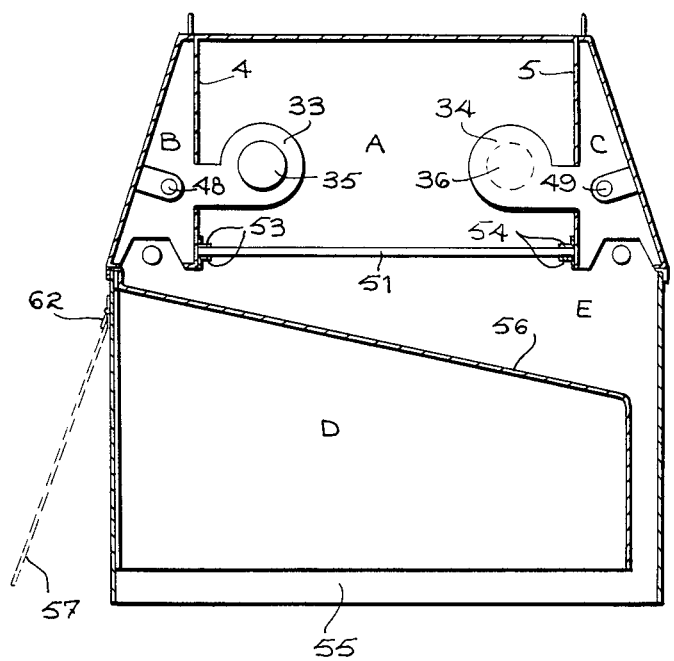

FIGS. 4 and 5 illustrate the air scrubber apparatus of FIG. 1 provided with four adjustable chain hangers for hanging up the housing thereof from the ceiling of the room, and with plexiglass panels thereunder which surround a volume located between the housing of the scrubber apparatus and the top surface of the work table; and FIGS. 6 and 7 show a second embodiment of the air scrubber apparatus of the invention differing from the first embodiment by the position of the means for killing germs, bacteria and the like present in the purified air, and by the structure of the air filter means, this second embodiment being provided with a plexiglass wall structure thereunder defining two distinct volumes in communication therebetween in the proximity of the top surface of the work table.

As illustrated on FIGS. 4 and 5 of the drawings the air scrubber apparatus comprises a housing designated generally by the reference numeral 1 which is hung up from the ceiling of for example an embalming or autopsy room above a work table disposed in this room by means of four adjustable chain hangers 2 attached respectively to one corner of a top surface 3 (see FIG. 6) of the housing 1.

Figure 2:
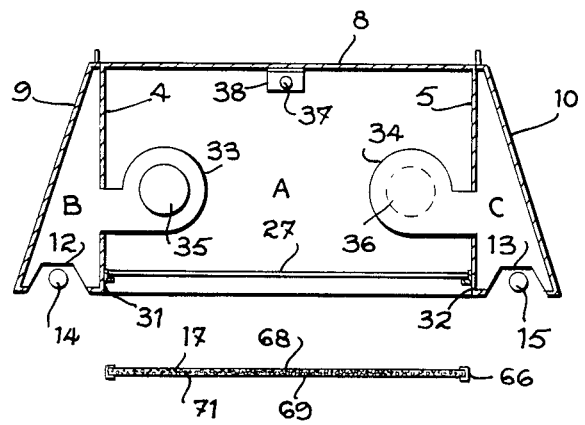
FIG. 2 is a cross sectional view of the air scrubber apparatus of FIG. 1.
Figure 3:
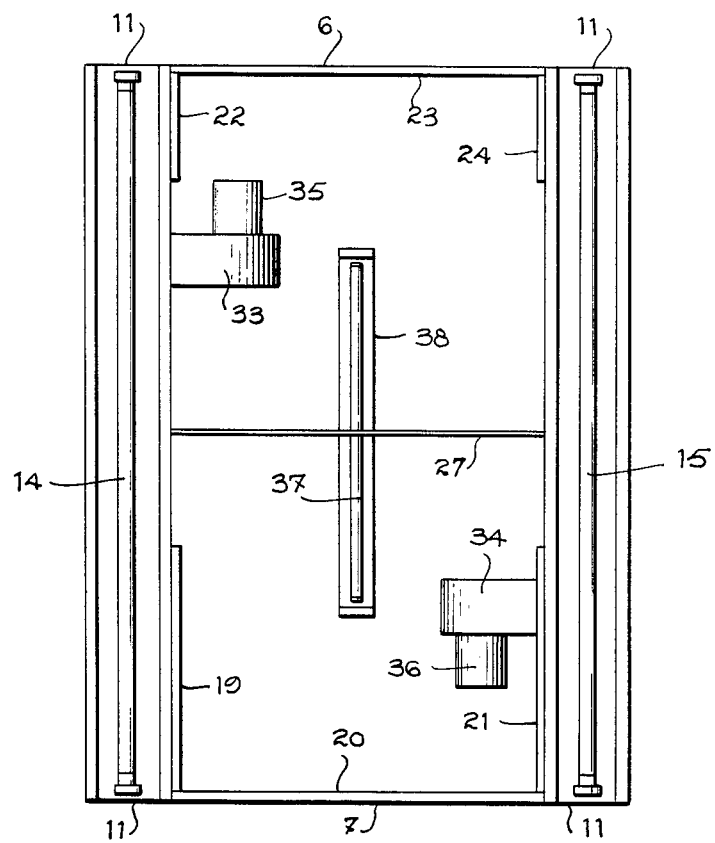
FIG. 3 is a bottom view of the air scrubber apparatus of FIG. 1.

Referring now to FIGS. 1 to 3 of the drawings, the housing designated generally by the reference numeral 1 is made of sheet material, for example stainless steel or aluminium. The housing 1 comprises a top wall 8, two inner side walls 4 and 5 and two end walls 6 and 7 defining a central compartment A. The housing 1 also comprises two outer side walls 9 and 10 which are formed as shown on FIGS. 1 and 2 and which define with the inner side walls 4 and 5, with four end walls 11 each located at a corresponding corner of the housing 1, and with bottom walls 12 and 13 a first longitudinal outer compartment B and a second longitudinal outer compartment C.

The bottom walls 12 and 13 constitute respectively a receptacle and reflector for cold white fluorescent tubes 14 and 15, which tubes provide sufficiently with light the top surface of the corresponding work table. As can be seen, the tube 14 is mounted under the first compartment B and the tube 15 is mounted under the second outer compartment C.

As shown on FIG. 1, the four end walls 11 are each provided with outlets to the room such as 16.

The bottom wall of the central compartment A is formed by two filter portions 17 and 18 each forming one half of such a bottom wall. For mounting these filter portions 17 and 18, metal supports 19, 20, 21, 22, 23 and 24 each formed with a 90° angle are fixed to the housing 1 as shown on FIGS. 1 to 3. As can be deduced from these three figures, the following procedure may be followed to mount the portions 17 and 18. In a first step, the filter portion 18 is positioned on the supports 19, 20 and 21. In a second step, the end 25 of this portion 18 is lifted to allow positioning of an holding part 26 so that a groove 28 of this holding part 26 is positioned on a rod 27 mounted transversally between the inner side walls 4 and 5, the rod 27 thereby maintaining in place the part 26. Thereafter the end 25 is released. In a last step, the filter portion 17 is introduced in the central compartment A and positioned on the supports 22, 23 and 24 and on the holding part 26. The structure of the filter portions 17 and 18 will be further elaborated hereinafter.

A metal mesh 29 provided with a frame 30 is mounted under the filter portions 17 and 18 and held in place by adjustment between the lower parts of the walls 4, 5, 6 and 7 below the supports 19 to 24 such as 31 and 32.

In operation, two exhaust fans 33 and 34 when driven through corresponding electrical motors 35 and 36, respectively, move the foul air, produced during for example an embalming or an autopsy carried out on the work table located under the housing 1, towards the interior of the central compartment A through the metal mesh 29 and the filter portions 17 and 18 for the purpose of purifying the moved foul air.

An ultraviolet <black light> fluorescent tube 37 is mounted inside the compartment A on the top wall 8 through an holding assembly 38 to kill germs, bacteria and the like present in the purified air in the central compartment A through its ultraviolet radiation.

The exhaust fan 33 transfers a first part of the purified air from the central compartment A to the first outer compartment B for a redistribution thereof in the room through the end outlets 16 of the compartment B, and the exhaust fan 34 transfers a second part of the purified air from the central compartment A to the second outer compartment C for a redistribution thereof in the room through the end outlets 16 of the compartment C.

As illustrated on FIG. 3 and for a proper operation of the scrubber apparatus, the exhaust fan 33 is located in a first half of the central compartment A while the exhaust fan 34 is located in the second half of this compartment A, thereby producing passage of foul air through the entire surface of the filter portions 17 and 18.

FIG. 1 shows a first switch 43 provided to energize the two fluorescent tubes 14 and 15, a second switch 41 with its associated indicating lamp 42 provided to energize the ultraviolet fluorescent tube 37, and a third switch 39 with its associated indicating lamp 40 provided to energize the two motors 35 and 36. Of course, the three fluorescent tubes 14, 15 and 37 are energized through corresponding ballasts which are not shown on the different Figures of the attached drawings.

As shown on FIGS. 4 and 5, the volume located between the housing 1 and the top surface of the work table disposed thereunder may be closed through a plexiglass panel structure 44 or 45 appropriately fixed to the housing 1 through parts 60 or 61 to reduce dispersion into the room of the malodorous, pungent and/or corrosive gaseous substances produced during, for example an embalming or an autopsy carried out on the work table. The panels of the structure (44 or 45) may be inclined (see 44 on FIG. 4) or vertical (see 45 on FIG. 5) depending on the dimensions of the top surface of the work table with respect to those of the housing 1. In both cases, the plexiglass panel structure is provided with a panel such as 46 or 47 preferably on each side of the work table, this panel 46 or 47 being fixed at its upper side to the remainder of the structure 44 or 45 through strap-hinges 58 or 59, for the purpose of allowing access to the interior of the plexiglass structure 44 or 45 and consequently to the top surface of the work table. The plexiglass panel structure 44 or 45 therefore increases the efficiency of the scrubber apparatus, when used with bad smelly cases and for contagious cases, etc., by allowing working in a bacteria free environment and with no bad odors.

Referring now to FIGS. 6 and 7 of the drawings, the ultraviolet <black light> fluorescent tube 37 located in the central compartment A (see FIGS. 2 and 3) may be replaced by a first ultraviolet <black light> fluorescent tube 48 mounted in the first outer compartment B and a second ultraviolet <black light> fluorescent tube 49 mounted in the second outer compartment C. The two tubes 48 and 49 kill more efficiently the germs, bacteria and the like present in the purified air.

The scrubber apparatus of FIGS. 6 and 7 also comprises an air filter 65 comprising a filter portion 51 and a part 50 giving an external drawer-like to the air filter 65. For the purpose of positioning the filter portion 51, the end wall 6 has an opening 52 therein and guides 53 and 54 mounted on the inner side walls 4 and 5 are provided. Of course, the filter portion 51 replaces both the filter portions 17 and 18 of FIG. 1 and is positioned by sliding thereof in the guides 53 and 54 through the opening 52.

Of course, the metal mesh 29 of FIG. 1 can still be mounted by adjustment between the guides 53 and 54 in the same manner as described above.

The scrubber apparatus of FIGS. 6 and 7 further comprises an outer plexiglass panel structure 55 similar to the structure 45 of FIG. 5 and provided with a panel 57 fixed to the remainder of the structure 55 through strap-hinges such as 62. An inner plexiglass panel structure 56 is also mounted inside the structure 55 around an opening open or closed through the panel 57, and defines a volume D in contact with the top surface of the work table and accessible through the opening corresponding to the panel 57. The inner structure 56 comprises three vertical panels having a lower end spaced from the work table thereby providing communication between the volume D and a volume E in contact with the filter portion 51. As can be seen, the only communication between on one hand the volume E, and on the other hand the volume D and the opening corresponding to the panel 57 is through the spacing between the top surface of the work table and the lower end of the vertical panels of the structure 56. When the exhaust fans 33 and 34 are in operation, it can be easily appreciated with reference to FIGS. 6 and 7 that the air in the volume D defined by the inner wall structure 56 is moved from this volume D to the filter portion 51 through the volume E and the spacing between the top surface of the work table and the lower end of the vertical panels of the inner structure 56. Such an inner structure 56 is particularly useful to move towards the filter portion 51 malodorous, pungent and/or corrosive geasous substances heavier than the air.

The structure of the filter portion 51 of FIGS. 6 and 7 and of the filter portions 17 and 18 of FIGS. 1 and 2 will now be described in details.

Each of these filter portions comprises a frame such as 66 and 67 (see FIGS. 1 and 2). Such a frame holds two sheets or for example polypropylene material such as 68 and 69 (see FIG. 2) provided with holes therein such as 70 (see FIG. 6) to allow passage of air therethrough. The volume defined between the sheets 68 and 69 is filled with pellets such as 71 (see FIG. 2) of a filtering material, which sheets 68 and 69 are of course substantially rigid.

This filtering material is a mixture of two compounds: potassium permanganate and aluminium oxide. More particularly, the pellets of filtering material are activated pellets of aluminium oxide ($Al_2O_3$) which are impregnated with potassium permanganate ($KMnO_4$), and constitute a very effective agent to clean the air from malodorous, pungent and/or corrosive gaseous substances. These gaseous substances comprise, for example, formaldehyde and all other odorous gases such as exhumation-floaters-gangrenous and other putrefactive gases, which are present during an embalming or autopsy.

It should be pointed out that potassium permenganate is an effective oxidation agent which has the capacity to break other substances into simpler and non smelling neutral substances, such as steam and carbonic acid. This function makes the filter portions 17, 18 and 51 effective against gaseous substances such as sulphur compounds, ethylene, ammonia, and formaldehyde.

Consequently, when the above defined foul air becomes in contact with the pellets of filtering material while passing through the filter portions 17, 18 and 51, it is purified very efficiently, as the above defined gaseous substances are removed from the air.

Of course, the efficiency of the filter portions is governed by parameters such as the quality of the filtering material, the size of the pellets, the thickness of the layer of pellets, the air speed through the filter portions, and extreme conditions of humidity or temperature.

The activated pellets of aluminium oxide impregnated with potassium permanganate are originally of a light lilac colour. During use thereof, the pellets change color. It is therefore easy to observe the speed at which the filtering material is consumed. The penetration depth can be observed by taking out a few pellets and breaking them against a hard surface. When the change of color has reached all the way into the core of the pellet, the filtering material has been used up and should be changed. The consumed pellet is inert and can be used as, for example, filling. The advantage is due to the fact that sorbed pollution has been broken up and dispersed.

If the operational conditions are always constant, the change of filling material can in future be done routinely at the same interval as was measured at the beginning, or perhaps at a shorter interval as a safety margin.

As the ultraviolet ray kills all germs and bacteria instantly, in addition to the fact that the permanganate is an excellent oxidizing agent, in many instances the recirculated air in the room is in better breathing condition than the ambient air from the outside.

As the scrubber apparatus treats the air into a closed circuit, the use of the scrubber apparatus does not increase the heating or conditioning costs as no heated or cooled air is evacuated to the outside.

The present invention has been hereinabove described with reference to preferred embodiments. However, it should be pointed out that any modification to these preferred embodiments within the scope of the appended claims is not deemed to change the concept and nature of the present invention.

We claim:

1. An air scrubber apparatus for purifying foul air produced during an embalming, an autopsy or the like carried out on a work table disposed in a room for embalming, autopsy or the like, comprising:

a housing positioned above the work table, said housing defining a first and a second outer compartment disposed substantially horizontally with respect to each other, said housing also defining a central compartment disposed between said first and second outer compartments, said central compartment being provided with bottom inlet opening means for said foul air, and said first and second outer compartments being each provided with outlets to said room which are located at predetermined positions;

air filter means positioned over said bottom inlet opening means of the central compartment, said filter means comprising a filtering material including aluminium oxide and potassium permanganate and being designed to allow passage of air therethrough, said filtering material which includes aluminium oxide and potassium permanganate purifying said foul air upon passage thereof through said filter means; and air pumping means for moving said foul air towards the interior of said central compartment through said filter means for the purpose of purifying said foul air, said pumping means comprising means for transferring the purified air from the central compartment to said first and second outer compartments in order to return the purified air to said room through said outlets, said predetermined positions of said outlets being selected so as to enable a redistribution of the purified air in said room.

2. The air scrubber apparatus of claim 1, further comprising means for killing germs, bacteria and the like present in said purified air.

3. The air scrubber apparatus of claim 2, wherein said killing means comprise an ultraviolet ray tube mounted in said central compartment.

4. The air scrubber apparatus of claim 2, in which said killing means comprise a first ultraviolet ray tube mounted in the first outer compartment and a second ultraviolet ray tube mounted in the second outer compartment.

5. The air scrubber apparatus of claim 1, wherein said filtering material comprises activated pellets of aluminium oxide which are impregnated with potassium permanganate.

6. The air scrubber apparatus of claim 1, wherein said air filter means comprise two sheets of substantially rigid material mounted parallel to each other, said two sheets being provided with holes therein to allow passage of said foul air therethrough and defining a space therebetween which is filled with said filtering material.

7. The air scrubber apparatus of claim 6, in which said substantially rigid material comprises polypropylene.

8. The air scrubber apparatus of claim 1, wherein said air filter means have an external drawer-like shape, said central compartment being provided with bottom guides and with an end comprising an opening therein to receive said air filter means having an external drawer-like shape for the purpose of positioning said air filter means over said bottom inlet opening means of the central compartment.

9. The air scrubber apparatus of claim 1, wherein said air filter means comprise a first portion corresponding to a first part of said bottom inlet opening means and a second portion corresponding to a second part of the bottom inlet opening means, said scrubber apparatus comprising means for positioning said first and second portions of the air filter means over said first and second parts of the bottom inlet opening means, respectively.

10. The air scrubber apparatus of claim 1, comprising an external mesh covering said air filter means.

11. The air scrubber apparatus of claim 1, wherein said work table has a longitudinal axis, and wherein said housing has a longitudinal axis substantially parallel to the longitudinal axis of the work table, and a first and a second end, said housing further comprising a first and a second inner walls both extending from said first end to said second end of the housing, said first inner wall forming a common wall of said central compartment and said first outer compartment, and said second inner wall forming a common wall of said central compartment and said second outer compartment.

12. The air scrubber apparatus of claim 11, wherein said central compartment comprises a first half corresponding to the first end of said housing and a second half corresponding to the second end of said housing, and wherein said air pumping means comprise first air pumping means mounted within said first half of the central compartment, and second air pumping means mounted within said second half of the central compartment, said first pumping means comprising means for transferring a first part of the purified air from the central compartment to the first outer compartment through the first inner wall, and said second pumping means comprising means for transferring a second part of the purified air from said central compartment to said second outer compartment through said second inner wall.

13. The air scrubber apparatus of claim 1, in which said central compartment comprises no bottom wall thereby providing said bottom inlet opening means, and wherein said air filter means has a wall-like structure to constitute a bottom wall of said central compartment.

14. The air scrubber apparatus of claim 1, comprising lighting means mounted under said first and second outer compartments.

15. The air scrubber apparatus of claim 11, wherein said first and second outer compartments each comprise two ends, and wherein said outlets are located at the two ends of said first and second outer compartments.

16. The air scrubber apparatus of claim 1, in which said room comprises a ceiling, said scrubber apparatus comprising means for hanging up said housing from the ceiling of said room.

17. The air scrubber apparatus of claim 1, comprising an outer wall structure made at least in part of transparent material, the work table comprising a top surface and said outer wall structure defining between said work table and said housing a substantially closed volume in contact with said top surface and said filter means, said outer wall structure being provided with access means in order to allow access for a user to said substantially closed volume and therefore to said top surface of the work table.

18. The air scrubber apparatus of claim 17, further comprising an inner wall structure also made at least in part of transparent material and located inside said outer wall structure, said inner wall structure defining within the substantially closed volume a first volume in contact with said access means and said top surface, and a second volume in contact with said air filter means, said inner wall structure being designed to provide communication between the first and second volumes in the proximity of said top surface of the work table.

19. The air scrubber apparatus of claim 17, in which said outer wall structure comprises a first wall formed at least in part by a panel mounted through strap-hinges, said panel mounted through strap-hinges constituting said access means.

* * * * *